United States Patent
Blischak et al.

(10) Patent No.: US 7,338,464 B2
(45) Date of Patent: *Mar. 4, 2008

(54) NON-CONSTANT PRESSURE INFUSION PUMP

(75) Inventors: Brian Blischak, Plano, TX (US); John H. Erickson, Plano, TX (US); Terry Daglow, Allen, TX (US); Sandra M. Hooper, Allen, TX (US); Bruce D. Wigness, Minneapolis, MN (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 839 days.

This patent is subject to a terminal disclaimer.

(21) Appl. No.: 10/626,902

(22) Filed: Jul. 25, 2003

(65) Prior Publication Data

US 2004/0153029 A1  Aug. 5, 2004

Related U.S. Application Data

(63) Continuation of application No. 09/796,969, filed on Mar. 1, 2001, now Pat. No. 6,620,151.

(51) Int. Cl.
*A61M 31/00* (2006.01)
*A61K 9/22* (2006.01)

(52) U.S. Cl. .................................. 604/65; 604/892.1

(58) Field of Classification Search ............ 604/890.1, 604/891.1, 892.1, 65–67, 207, 245–249
See application file for complete search history.

(56) References Cited

U.S. PATENT DOCUMENTS

| 3,731,681 | A |   | 5/1973  | Blackshear et al. |
|-----------|---|---|---------|-------------------|
| 3,946,731 | A |   | 3/1976  | Lichtenstein      |
| 3,951,147 | A |   | 4/1976  | Tucker et al.     |
| 4,077,405 | A | * | 3/1978  | Haerten et al. ............... 604/66 |
| 4,299,220 | A |   | 11/1981 | Dorman            |
| 4,370,983 | A |   | 2/1983  | Lichtenstein      |
| 4,443,218 | A |   | 4/1984  | DeCant, Jr. et al. |
| 4,772,263 | A |   | 9/1988  | Dorman et al.     |
| 4,836,752 | A | * | 6/1989  | Burkett ........................ 417/12 |
| 4,838,887 | A |   | 6/1989  | Idriss            |
| 5,006,997 | A |   | 4/1991  | Reich             |
| 5,342,404 | A | * | 8/1994  | Alt et al. ........................ 607/6 |
| 6,129,702 | A | * | 10/2000 | Woias et al. .................. 604/65 |
| 6,986,753 | B2 | * | 1/2006 | Bui ............................. 604/31 |

* cited by examiner

*Primary Examiner*—Matthew F. DeSanto
(74) *Attorney, Agent, or Firm*—Christopher S. L. Crawford; Peter Lando; Melissa Acosta (57) ABSTRACT

The present invention relates to an implantable infusion pump having a refillable infusate reservoir in fluid communication with a delivery site via a flow path. This flow path includes a flow resistance. The infusion pump includes a sensing device(s), positioned relative to the flow path, to provide data regarding a flow rate along the flow path. The infusion pump effects a division of a total flow period into at least a plurality of unit dose periods, each unit dose period effecting delivery of a unit dose of infusate. The cumulative effect of delivering the total number of unit dose periods is the delivery of a desired dose over the total flow period. The present invention permits a reservoir pressure to vary over any portion of total flow period but effects a constant-pressure state over each unit dose cycle.

9 Claims, 9 Drawing Sheets

NON-CONSTANT PRESSURE INFUSION PUMP

CROSS-REFERENCE TO RELATED APPLICATIONS

The present invention is a continuation of, and hereby claims priority to, copending and commonly assigned U.S. patent application Ser. No. 09/796,969 entitled "Non-Constant Pressure Infusion Pump," filed Mar. 1, 2001, now U.S. Pat. No. 6,620,151, the disclosure of which is hereby incorporated herein by reference.

FIELD OF THE INVENTION

The present invention relates to an implantable infusion pump, and in particular, to an infusion pump capable of effecting a precisely controlled (constant or variable) fluid flow delivery rate, independent of a constant reservoir pressure.

BACKGROUND OF THE INVENTION

Modern implantable infusion devices, or implantable pumps, for delivering an infusate (e.g., medicaments, insulin, etc.) commonly have a rigid housing that maintains a collapsible infusate reservoir. The housing includes a needle-penetrable septum that covers a reservoir inlet. A flow passage is provided between the reservoir and an exterior surface of the device. At the flow passage outlet, a flexible delivery catheter is provided.

These devices are implanted at a selected location in a patient's body so that (i) the inlet septum is proximate to the patient's skin and (ii) a distal end of the catheter is positioned at a selected delivery site. Infusate can then be delivered to the infusion site by controlling the flow of such fluid from the device infusate reservoir into the delivery catheter. When the infusate reservoir becomes empty, the reservoir is refillable through the reservoir inlet by injecting a new supply of infusate through the apparatus' inlet septum. Due to the location of the device in relation to the skin of the patient, injection can be readily accomplished using a hypodermic needle (or cannula).

Infusate is expelled from the reservoir to an infusion site by collapsing the reservoir. Some infusion pumps use an electrically powered mechanism to "actively" pump infusate from the infusate reservoir into the delivery catheter. Examples of these types of "active pumping" devices include so-called peristaltic pumps (e.g., SynchroMed® implantable pump from Medtronic, Inc., Minneapolis, Minn.) and accumulator-type pumps (e.g., certain external infusion pumps from Minimed, Inc., Northridge, Calif. and Infusaid® implantable pump from Strato/Infusaid, Inc., Norwood, Mass.). These devices have certain advantages; however, such devices have a large disadvantage in that they use relatively large amounts of battery power to effect infusion. Given that batteries tend to add bulk and weight and their replacement requires surgical intervention, it is very desirable to minimize power consumption in implantable infusion pumps.

Another type of implantable pump that is typically much more electrically efficient uses a passive pumping mechanism. In fact, certain of these devices can be constructed and operated without any electrical power at all. A passive pumping mechanism generally consists of a means of pressurizing the infusate reservoir and a means of rstricting the fluid flow. All of these devices operate under the principle that the fluid flow rate (Q) is directly proportional to a pressure difference ($\Delta P$) between the infusate reservoir interior and the delivery site and inversely proportional to the total flow resistance provided by the fluid passage and delivery catheter (collectively (R)), wherein $$Q = \Delta P \div R$$

A practical pump must have a predictable flow rate (Q). To achieve this goal, conventional designs have strived to develop substantially constant pressure sources.

The first means of developing such a "constant pressure source" includes using a two-phase fluid, or propellant, that is contained within the rigid housing and is further confined within a fluid-tight space adjacent to the infusate reservoir. Pumps constructed in this manner are called "gas-driven" pumps.

The propellant is both a liquid and a vapor at patient physiological temperatures, e.g., 98.6° F., and theoretically exerts a positive, constant pressure over a full volume change of the reservoir, thus effecting the delivery of a constant flow of infusate. When the infusate reservoir is expanded upon being refilled, a portion of such vapor reverts to its liquid phase and thereby maintains a state of equilibrium between the fluid and gas states at a "vapor pressure," which is a characteristic of the propellant. The construction and operation of implantable infusion pumps of this type are described in detail, for example, in U.S. Pat. Nos. 3,731,681 and 3,951,147. Pumps of this type are commercially available, for example Model 3000™ form Arrow International, Reading, Penn. and IsoMed® from Medtronic, Inc., Minneapolis, Minn.

Gas-driven infusion pumps typically provide an electrically efficient means to deliver a flow of infusate throughout a delivery cycle. However, such infusion pumps depend upon a constant pressure source, wherein the output fluid flow rate is directly proportional to a propellant-reservoir pressure. If the propellant-reservoir pressure varies, then so will the fluid flow rate and the drug delivery rate.

The propellant-reservoir pressure of conventional gas-driven infusion pumps are susceptible to changes in ambient temperature and pressure. This, in turn, makes the fluid flow rate such devices susceptible to changes in ambient temperature and pressure. Such changes in drug infusion rates are undesirable and, in certain situations, unacceptable.

Circumstances readily exist where either ambient temperature or pressure can rapidly change a significant amount. For example, the reservoir pressure of some conventional gas-driven pumps can change as much as 0.5 psi for each 1° F. change in body temperature. Thus, for example, assuming a pump driving force of 8 psi at 98.6° F., a fever of only 102.6° F. can result in a twenty-five percent (25%) increase in propellant-reservoir pressure and thus, a corresponding (or larger) increase in an fluid flow rate. In addition, changes in environmental temperature affect the infusate viscosity as well as the vapor pressure produced by the propellant, thereby further increasing the pump's susceptibility to temperature.

An even more serious situation results from changes in ambient pressure. Although minor variations in ambient pressure at any given location on earth may not significantly affect delivery flow rates, with modern modes of transportation, a patient can rapidly change altitude during travel, such as when traveling in the mountains or when traveling by plane. In a like manner, a patient can experience a rapid change in pressure when swimming or diving.

The rigid housing of the conventional, gas-driven infusion pump provides an absolute constant-internal pressure ($P_R$) (at constant temperature) independent of external pressures. However, largely due to compliance by the lungs and venous circulatory system, hydrostatic pressure within the human body closely follows ambient pressure ($P_D$).

The net effect is that the pressure differential ($\Delta P = P_R - P_D$) in conventional gas-driven pumps changes linearly with ambient pressure. Consequently, a delivered infusate flow rate can increase as much as forty percent (40%) when a patient takes a common commercial airline flight.

To overcome these practical circumstances, some conventional gas-driven infusion devices have been provided with elevated reservoir pressures. The increased reservoir pressures are not intended to prevent variations in a constant pressure delivery but are intended to mitigate their effect. In particular, for any given change of pressure, the effect on flow rate is effectively lessened if the total percentage of pressure change (relative to the reservoir pressure) can be reduced. These infusion devices possess undesirable attributes in that refilling operations are more difficult and the high-pressure vessels, which form the pump housing structures, must necessarily be stronger and are therefore more susceptible to manufacturing problems.

Another method of attempting to produce a constant pressure source and thereby more accurately controlling a rate of fluid delivery is to incorporate a pressure regulator, such as that disclosed in U.S. Pat. No. 4,299,220. The pressure regulator described therein, which is positioned between the infusate reservoir and delivery catheter, uses a diaphragm valve to maintain a constant pressure differential (OP) across the fluid flow restrictor. In addition to increasing the operational complexity of such a pump mechanism and the volume of a fluid path extending therethrough, the pressure regulator may, depending upon device configuration, subject infusate solutions to high local shear stresses, which may alter the chemical or therapeutic properties of certain infusates.

An alternative method for attempting to produce a constant pressure source and thereby more accurately controlling a rate of fluid delivery, as well as addressing the susceptibilities of the two-phase pumps to ambient temperature and pressure, is proposed in U.S. Pat. No. 4,772,263. Specifically, in place of the conventional rigid enclosure that maintains a two-phase fluid, the disclosure teaches forming the fluid reservoir between a rigid portion (which maintains at least the inlet septum) and a flexible drive-spring diaphragm. The spring diaphragm is exposed to the body of the patient and the pressure therein. The spring diaphragm creates a more desirable "relative" (as opposed to an absolute) pressure source. By exposing the spring diaphragm to the pressures inside the body it is possible for the pump to respond and react to changes in ambient pressure so that AP is unaffected. Likewise, it is possible to construct the spring diaphragm so that the pressure that it generates is not affected by changes in ambient temperature. While this configuration offers practical performance advantages, this design offers a unique configuration that may not be adopted by all constant flow pump designs.

Accordingly, a need exists for an electrically efficient system to enable a controllable (constant or variable) fluid flow delivery rate independent of either a constant reservoir pressure or external conditions that may otherwise result in undesirable or unpredictable output fluid flow variations.

SUMMARY OF THE INVENTION

An object of the present invention is to provide an implantable infusion device with a non-constant reservoir pressure (over at least a portion of the flow cycle) that controls fluid flow across a fluid flow restrictor (with or without other fluid control elements) by dividing a greater dose cycle into a series of (smaller) unit dose cycles over which the reservoir pressure is substantially constant.

Another object of the present invention is to provide an electrically efficient implantable infusion device, having a convenient pressure reservoir, that is capable of delivering a prescribed dosage of a fluid infusate independent of either a constant reservoir pressure, ambient temperature or pressure, changes in device performance, or infusate properties.

Another objective of the present invention is to provide an implantable infusion device that is simpler in construction.

The present invention is directed to a controlled-rate infusion device for implantation in a living body. The infusion device includes a collapsible infusate chamber, an energy source to collapse the chamber, and an outlet flow path extending between the chamber and a device outlet. The infusion device further includes at least one flow restrictor, a controller, at least one valve or variable flow restrictor to selectively alter a flow resistance of the outlet flow path, and at least one pressure sensing device. The pressure sensing device(s) are positioned relative to the outlet flow path as well as about the flow resistance (i.e., any combination of flow restrictors and/or valves). The controller is adapted to control an operation of the valve (or variable flow restrictor) based on measured value(s) obtained by the pressure sensing device(s).

In another aspect, the present invention is directed to a controlled-rate infusion device for implantation in a living body. The infusion device includes a collapsible infusate chamber, an energy source to collapse the chamber, and an outlet flow path extending between the chamber and a device outlet. The infusion device further includes a controller, a valve (or variable flow restrictor) to selectively obstruct the outlet flow path, and one or more pressure sensing devices. The pressure sensing devices are positioned relative to the outlet flow path as well as about the flow resistance. The controller is adapted to assess whether output flow from the device is undesirably restricted based on measured values obtained from the pressure sensing devices.

Another aspect of the present invention is directed to a method for controlling infusate output from an implantable-infusion device for a prescribed dose period. The device includes a collapsible infusate chamber, an energy source to collapse the chamber, and an outlet flow path extending between the chamber and a device outlet, and the outlet flow path includes a restrictor network, which includes an occlusion in the outlet flow path. The method includes the steps of: (i) dividing the prescribed dose period into a plurality of unit dose periods, wherein each unit dose period is defined by an open-close cycle of the valve; and (ii) modifying a duty cycle of the open-close cycle of the valve so as to maintain a prescribed output volume (i.e., a unit dose) for each unit dose period.

Another aspect of the method for controlling infusate output from an implantable infusion device can include, independent of or in cooperation with other aspects of this method, measuring an infusate pressure differential across the restrictor network (or a portion thereof). Thus, the step of modifying the duty cycle is performed in accordance with a measured infusate pressure differential.

Another aspect of the method for controlling infusate output from an implantable infusion device can include, independent of or in cooperation with other aspects of this method, actuating the valve so as to effect a change in an occluded state of the outlet flow path. During or proximate to such actuation, a transient pressure profile on one side of the valve is measured, thus enabling an assessment of the performance of the valve, fluid path, flow restrictor and any other elements of the flow control system or flow path.

Another aspect of the method for controlling infusate output from an implantable infusion device can include, independent of or in cooperation with other aspects of this method, measuring an infusate temperature. Thus, the step of modifying the duty cycle is performed in accordance with a measured infusate temperature.

Another aspect of the present invention is that an output flow rate of a controlled rate pump can be changed by "resetting," or programming, such output flow rate. This resetting operation can be accomplished using non-invasive (e.g., magnetic switch, radio-frequency telemetry) or invasive methods (e.g., transcutaneous trocar). In this way, the methods and devices described herein can be used to construct a programmable pump, the flow rate of which can be manually or automatically (responsive to a clock, sensor, or other data input) modified to any of various beneficial patterns.

Other objects and advantages of the present invention will be apparent to those of ordinary skill in the art having reference to the following specification together with the drawings.

BRIEF DESCRIPTION OF THE DRAWINGS

In the drawings, like reference numerals and letters indicate corresponding parts throughout the several illustrations.

DETAILED DESCRIPTION OF THE PREFERRED EMBODIMENTS

Various embodiments, including preferred embodiments, will now be described in detail below with reference to the drawings.

Figure 1:
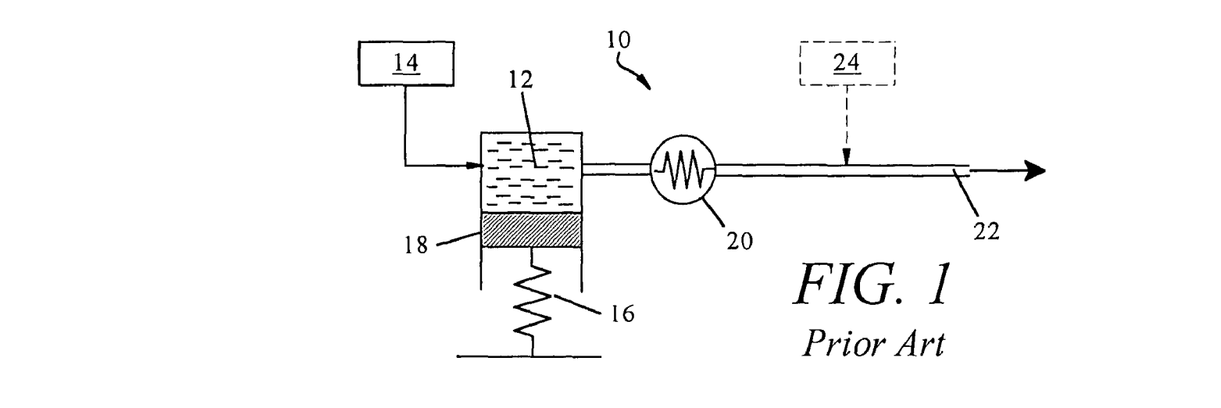
FIG. 1 schematically illustrates a conventional implantable infusion device for delivering an infusate at a prescribed rate incorporating a passive pumping mechanism.

FIG. 1 illustrates a conventional, constant flow rate infusion device 10. The device 10 is characterized by an infusate reservoir 12 that is required to store a prescribed volume of infusate, e.g., insulin, medicament, pain relieving drugs, etc. The infusate reservoir 12 is of sufficient volume so as to provide a supply of infusate (i.e., a prescribed dose (D)) over a flow period ($\tau$) at a (theoretically) constant flow rate. As but one possible example, the volume of the infusate reservoir 12 can be fixed at any prescribed volume to enable delivery of a precisely controlled volume of infusate from one day to more than three months. The infusate reservoir 12 can be refilled through a septum 14.

Infusate is pressurized and thereby driven from the infusate reservoir 12 by a drive source 16. The physical nature of the drive source 16 can be a two-phase fluid, which is confined between the housing of the device 10 and a movable diaphragm structure 18, a drive spring that forms the diaphragm structure 18, or like mechanisms/structures that develop a substantially constant pressure. A flow restrictor 20 is positioned downstream from the infusate reservoir 12 to establish an output flow rate. The flow restrictor 20 can be constructed of any number of potential structures, for example, a plate having a groove formed therein, capillary tubing, an etched flow chip, or the like. Although not shown, a filter is preferably interposed between the infusate reservoir 12 and the restrictor 20 to prevent any bacteria present in the infusate reservoir 12 from being transferred into the body, and to a certain extent, to protect the restricted flow path defined by the restrictor 20. Flow from the flow restrictor 20 is passed to a catheter 22 having its distal end positioned at a site for fluid delivery.

Conventional implantable infusion devices can further include a bolus port structure 24. The bolus port structure 24, whether integral with the device 10 or separate therefrom, provides direct fluid communication with the catheter 22. The bolus port structure 24 is adapted to receive independently a hypodermic needle (or cannula). Fluid delivered to the bolus port structure 24 can be used to flush the downstream catheter 22, deliver a prescribed dosage of medicament (possibly of a volume greater or at a rate greater than that otherwise capable to be delivered through the flow restriction 20), or perform troubleshooting or diagnostic procedures. Depending on the configuration of the bolus port structure 24, the structure 24 can also allow extraction of fluid from the patient via the catheter 22.

Figure 2A:
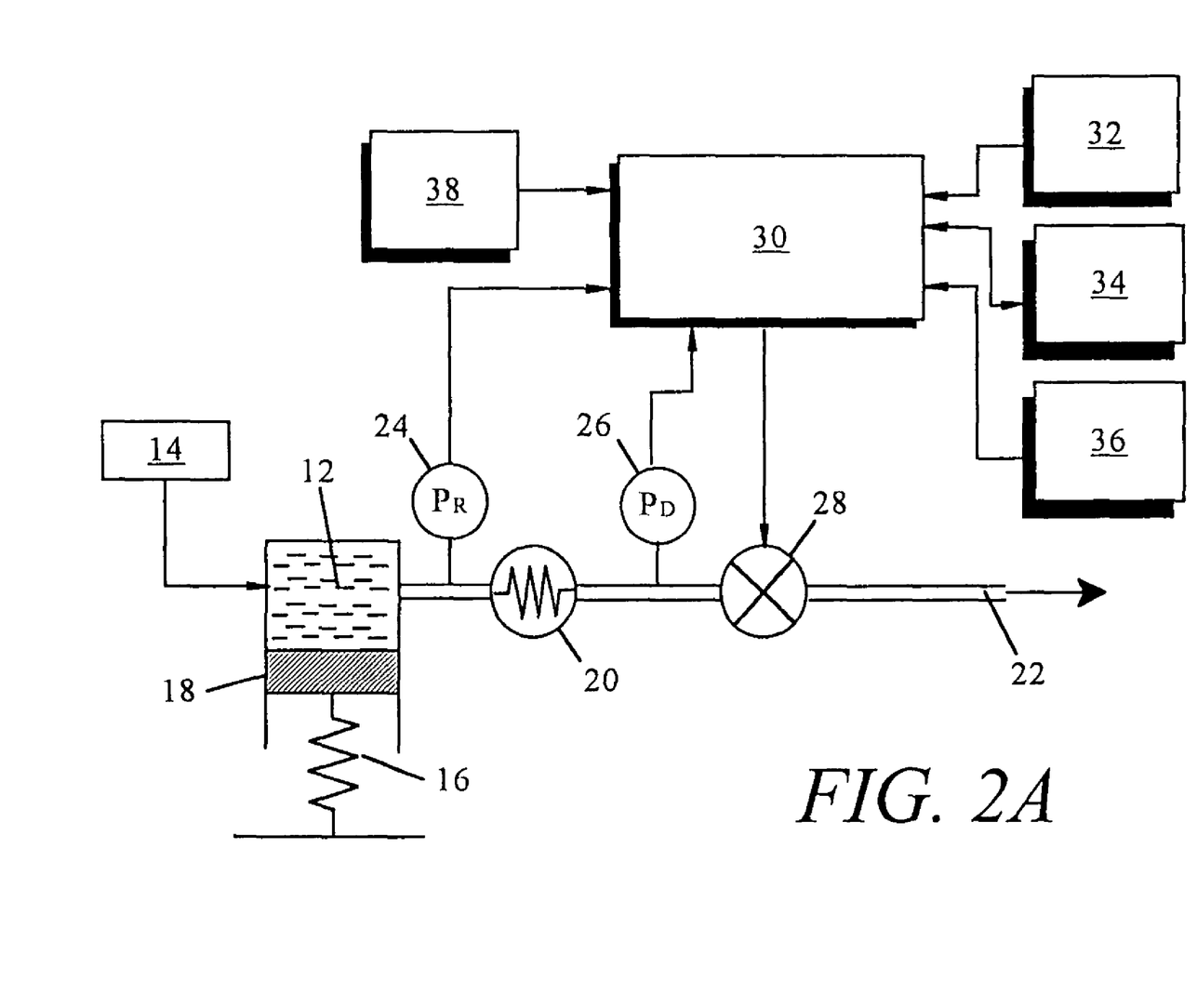
FIG. 2A schematically illustrates an implantable infusion device in accordance with one embodiment of the present invention, FIG. 2B schematically illustrates an implantable infusion device in accordance with another embodiment of the present invention, and FIG. 2C schematically illustrates an implantable infusion device in accordance with another embodiment of the present invention.
Figure 2B:
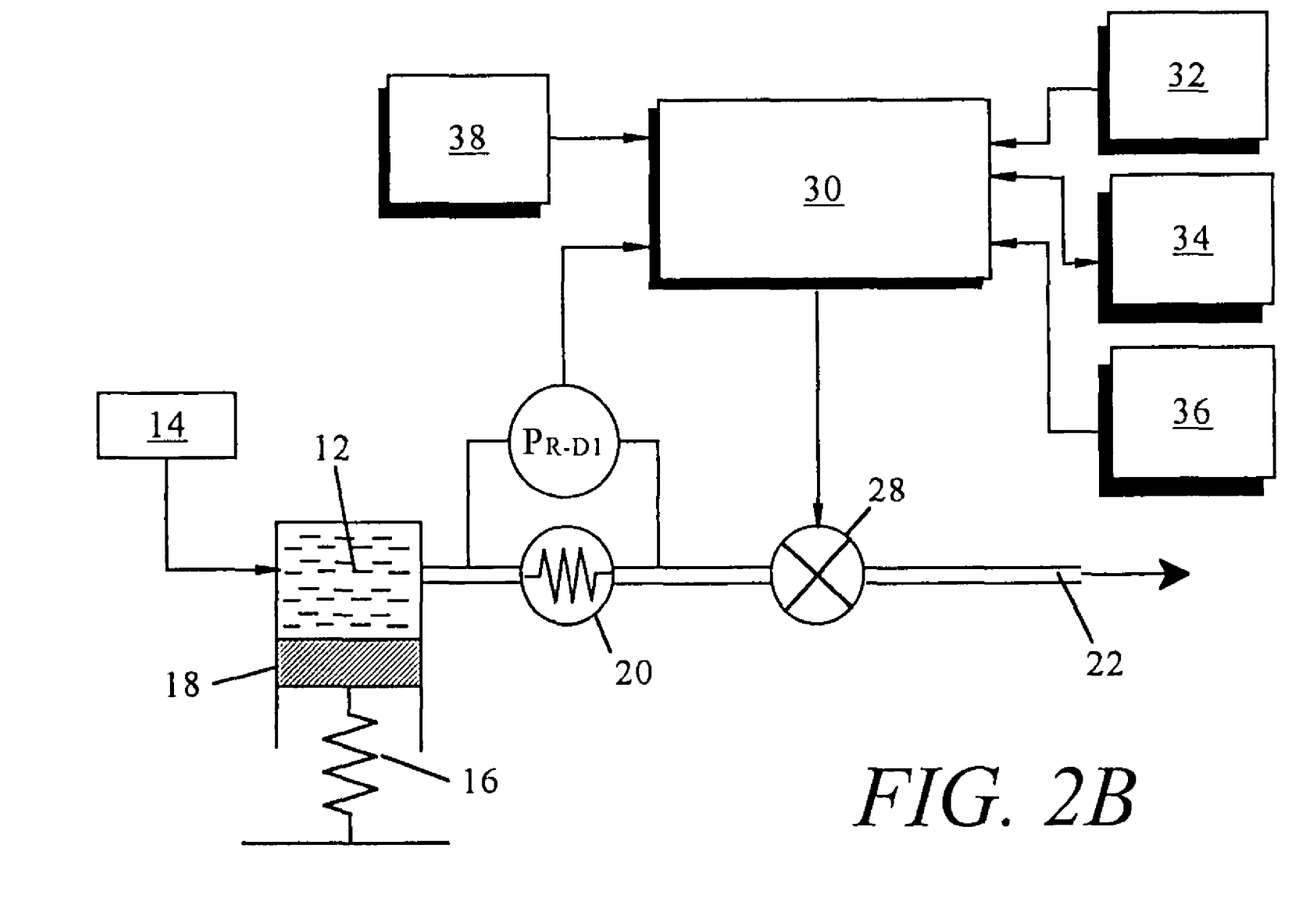
Figure 2C:
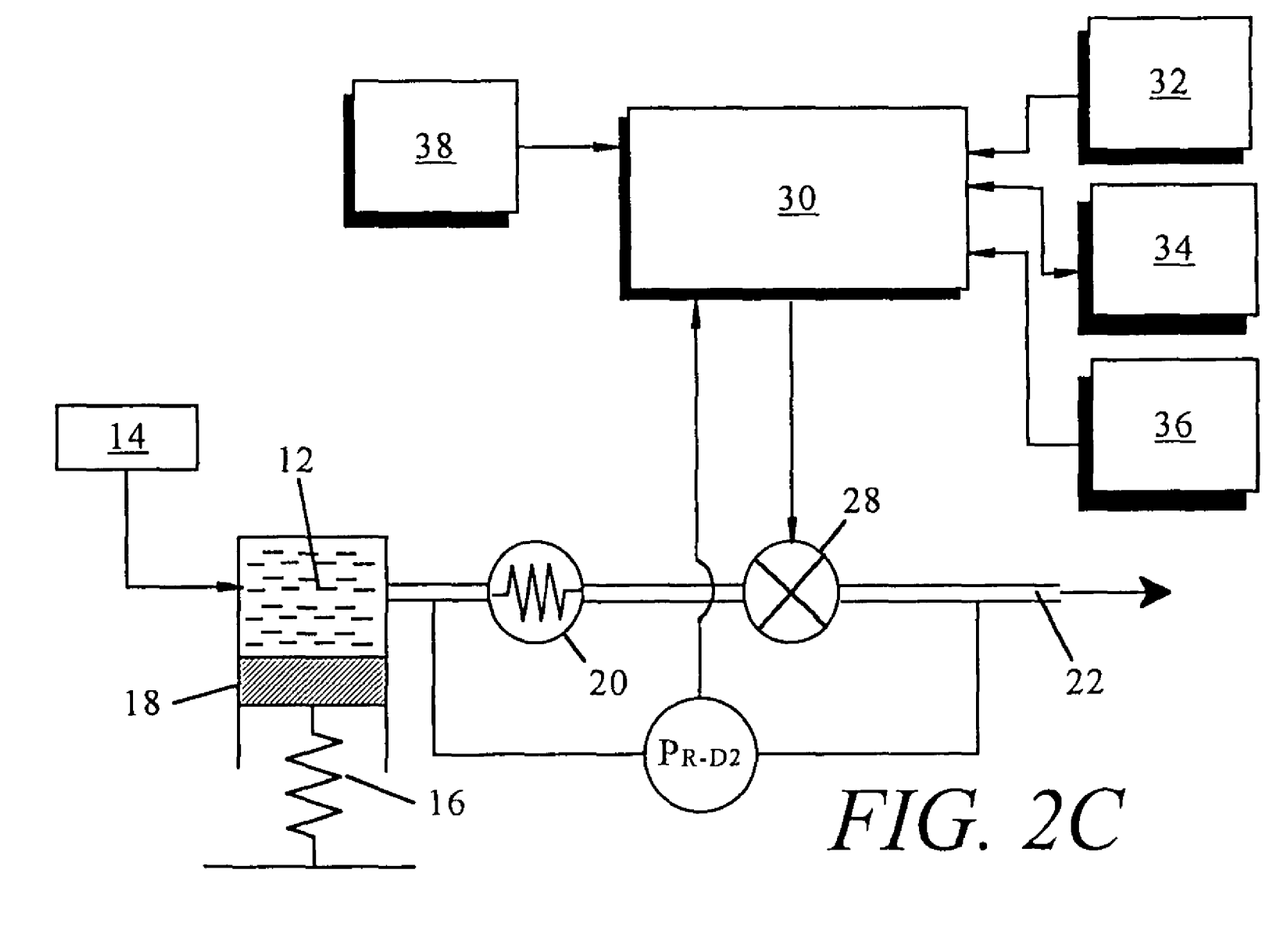

FIG. 2A illustrates one embodiment of the present invention. Specifically, an implantable infusion device has a infusate reservoir 12 connected between a septum 14 and a flow restrictor 20. Infusate within the infusate reservoir 12 is pressurized and thereby driven through the flow restrictor 20 by the drive source 16. The illustrated infusion device includes a first pressure sensing device 24, to measure a pressure upstream of the flow restrictor 20, and a second pressure sensing device 26, to measure a pressure downstream of the flow restrictor 20. Respective positions of the pressure sensing devices 24 and 26 relative to a flow path through the infusion device are not critical so long as the pressure sensing device 24 remains upstream of the flow restrictor 20 and the pressure sensing device 26 remains downstream of the flow restrictor 20. Alternatively, given that the flow rate will be determined by a pressure differential (ΔP) at the point of the pressure sensing devices 24 and 26, it is also possible to measure this pressure differential (ΔP) with a single pressure transducer, operatively coupled to the flow path at or about the same two points as otherwise occupied by the pressure sensing devices 24 and 26 (FIG. 2A or FIG. 4) or as otherwise occupied by the pressure sensing devices 24 and 40 (FIG. 4), as illustrated in FIGS. 2B and 2C.

It will be readily apparent to those of ordinary skill in the art that a multitude of configurations are within the scope of the present invention, such configurations including at least one flow restrictor, one pressure sensor, and a mechanism to change the total flow resistance of the system. To this end, FIGS. 2A to 11 illustrate some of the possible configuration-combinations that includes: (i) one or more flow restrictors arranged in parallel, series, or combinations thereof; (ii) one or more valves, whereby these elements can affect an overall flow resistance; and (iii) one or more pressure sensors that are capable of determining a pressure difference across any portion of or all of the flow restrictors or valves. In regard to (ii) above, depending upon the intended use of the infusion device, it may be desirable to use fixed or variable flow restrictors, which includes mono-stable, bi-stable, or multi-stable valves that have the potential of occluding or partially occluding the possible flow paths.

A valve 28 is positioned downstream of the flow restrictor 20, and is preferably positioned downstream of the pressure sensing device 26. Accordingly, the pressure sensing device 24 can be 24 can be positioned within or proximate to the infusate reservoir 12, and the pressure sensing device 26 can be positioned subsequent to the valve 28.

A controller 30 (e.g., a microprocessor) is electrically connected to the pressure sensing device 24, the pressure sensing device 26, and the valve 28. The controlled 30 functions to control fluid flow through the valve 28 based on respective outputs form pressure sensing devices 24 and 26.

A fluid flow rate across the flow restrictor 20 can be calculated from:

$$Q=(P_R-P_D)\div R$$

where,

Q is a flow rate output from the catheter 22;

$P_R$ is a measured reservoir pressure;

$P_D$ is a measured delivery pressure; and

R is a flow resistance value of the flow path as a whole, which can be approximated by the resistive value of the flow restrictor 20 (when the valve is in an open state).

An optional temperature sensing device 38 can also be coupled to the controller 30. If provided, the controller 30 would function to control fluid flow through the valve 28 also in consideration of (or solely based on) an output from the temperature sensing device 38. The controller 30 is adapted to relate changes in an infusate temperature to proportional changes in system pressure and/or to changes in the resistive value (R), the latter being caused by a change in fluid viscosity due to a change in infusate temperature. This ability of the controller 30 is managed by algorithm or look-up tables stored in memories 32 and/or 34.

A flow cycle of an infusion device is considered to extend through the delivery of the contents of the infusate reservoir 12, i.e., from a refilling event until a subsequent refilling event. The quantity (S) of active pharmacological agents or other agents (individually or collectively "agent") contained in the infusate reservoir 12 depends upon the fluid volume (V) of the infusate reservoir 12 and the concentration of the agent in the infusate stored therein:

$$S=V*C$$

where,

S is the quantity (e.g., mg) of the agent,

C is the agent concentration in the infusate contained in the infusate reservoir 12, and V is the fluid volume of the infusate reservoir 12.

The duration of the flow cycle is referred to as the flow period (τ). As is probable, the flow period will typically be between 1 and over three (3) months. It is related to the flow rate (Q) and the infusate reservoir volume (V) as follows:

$$\tau=V\div Q$$

where,

τ is the flow period (e.g., days), and

Q is the infusate flow rate (e.g., ml/day).

A prescribed (or desired) dose (D) delivered must be further calculated in accordance with the following:

$$D=Q*C$$

where,

D is the quantity of an agent delivered per unit of time (e.g., mg/day).

As discussed above, conventional constant flow infusion devices deliver a single prescribed dose (D) based on the assumption that a constant pressure is maintained over an entire flow period (τ). As also discussed above, this assumption can be realistically compromised by changes in ambient pressure or temperature, patient position, or infusate volume residing in the reservoir throughout a flow period (τ). Moreover, the total flow resistance (R) provided by the flow path can change over the lifetime of the infusion device further affecting the discharge performance of the device. Moreover, the properties of the infusate can change over the lifetime of the infusion device, further affecting the therapy.

In contrast, the devices of the present invention seek to provide the desired flow accuracy in spite of the fact that the pressure differential (ΔP) and/or flow resistance (R) may not remain constant over the entire flow period (τ). These devices do this by subdividing the flow period (τ) into smaller unit dose periods ($t_{i,j}$) over which the flow parameters (ΔP) and (R) are likely to remain constant and delivering the total dose (D) though a series of sequential unit dose periods ($t_{i,j}$). The following definitions and equations help to understand the present invention.

A flow period (τ) can be subdivided into any number (n) of prescribed dose periods ($T_i$), which may or may not be of equal duration. For conventional constant flow pumps, n=1. For the present invention, "n" may be any integer, preferably two or greater.

$$\tau = \sum_{i=1}^{n} T_i$$

For various embodiments of the present invention, the duration of the prescribed dose periods ($T_i$) may or may not be physician-alterable (i.e., to create a programmable pump) and/or patient-alterable (i.e., to create a programmable pump with patient-controllable elements) either before or during the flow period ($\tau$).

During each of the prescribed dose periods ($T_i$) a prescribed dose ($D_i$) is delivered. If all of these prescribed doses ($D_i$) are equal, then the equations describe a constant flow infusion device, possibly with improved flow accuracy such as, for example, illustrated in FIG. 2A. If these are multiple prescribed doses ($D_i$) of different magnitudes, then the equations describe a programmable pump operating with a complex continuous infusion pattern. The therapeutic value of theses complex infusion patterns is readily apparent to clinicians, and varies depending upon the agent, patient, and application.

In all applications, a certain quantity of drug ($s_i$) is to be delivered in the dose period ($T_i$) at a prescribed dose ($D_i$). The following equations illustrate the relationship among these variables, $$S = \sum_{i=1}^{n} s_i = \sum_{i=1}^{n} D_i * T_i$$

In the present invention, each of the prescribed dose periods ($T_i$) is further divided into any number ($m_i$) of unit dose periods ($t_{i,j}$). For the present invention, "m" may be any integer, one or greater. In a preferred embodiment, all of the unit dose periods ($t_{i,j}$) within a given prescribed dose period ($T_i$) are equal. This simplifies the calculations necessary for device operation; however, this is not a necessary condition. In general, $$T_i = \sum_{j=1}^{m_i} t_{i,j}$$

and, $$\tau = \sum_{i=1}^{n} \sum_{j=1}^{m_i} t_{i,j}$$

when all unit dose periods ($t_{i,j}$) within each of the prescribed dose periods ($T_i$) are equal, $$T_i = m_i * t_i$$

and $$\tau = \sum_{i=1}^{n} m_i * t_i$$

During each unit dose period ($t_{i,j}$), the valve 28 will be actuated through one complete cycle, such that it is in one position (i.e., designated open) for a fraction of the unit dose period ($t_{i,j}$) and in a second position (i.e., designated closed) for the balance of the unit dose period ($t_{i,j}$). Those skilled in the art will readily appreciate that it would also be possible to use one or more valves to move between two or more position during any given unit dose period ($t_{i,j}$), and it would also be possible for such valve(s) to move between different positions during the same or different unit dose periods ($t_{i,j}$).

In the simplified embodiment described herein, the controller 30 determines a timing for keeping the valve 28 in an open state based on the most recent estimate or measurement of the flow parameters ($\Delta P_{i,j}$) and ($R_{i,j}$). The flow parameters are assumed (approximated) to be constant for at least the period of time that the valve 28 remains in a given position. The following equations are useful in determining the amount of agent delivered ($s_i$) in a prescribed dose period ($T_i$), and the prescribed dosage pharmacologically perceived, $$t_{i,j} = t_{i,j\ open} + t_{i,j\ close}$$

$$S_i = C * \sum_{j=1}^{m_i} (t_{i,j\ open} * Q_{i,j\ open} + t_{i,j\ close} * Q_{i,j\ close})$$

$$D_i = (C \div T_i) * \sum_{j=1}^{m_i} (t_{i,j\ open} * Q_{i,j\ open} + t_{i,j\ close} * Q_{i,j\ close})$$

where $t_{i,j\ open}$ is the duration of time that the valve 28 is in an open state, $t_{i,j\ close}$ is the duration of time that the valve 28 is in a closed state, $Q_{i,j}$ open is the flow rate when the valve 28 is in the open state during unit dose period $t_{i,j}$, and $Q_{i,j\ close}$ is the flow rate when the valve 28 is in the closed state during unit dose period $t_{i,j}$.

For passive pumping devices, the flow rate can be further described by the following equations, $$Q_{i,j\ open} = \Delta P_{i,j\ open} \div R_{i,j\ open}$$

$$Q_{i,j\ close} = \Delta P_{i,j\ close} \div R_{i,j\ close}$$

For restrictor-based passive pumping devices, $\Delta P_{i,j\ open}$ will often be assumed to be equal to $\Delta P_{i,j\ close}$ for any given i,j. Thus, the position of the valve 28 simply changes the resistance magnitude (R) from $R_{i,j\ open}$ to $R_{i,j\ close}$. For passive pumping devices incorporating a regulator, $R_{i,j\ open}$ will often be approximated as equal to $R_{i,j\ close}$ and the position of the valve 28 simply changes the magnitude of $\Delta P$ from $\Delta P_{i,j\ open}$ to $\Delta P_{i,j\ close}$.

While in many cases $Q_{i,j\ close}$ will be a zero value, i.e., the valve 28 closes completely and flow stops, such is not a necessary condition. For example, if maintaining the valve is an open state uses battery power, then it may be advantageous to design the infusion device to have a non-zero $Q_{i,j\ close}$ flow rate to thereby reduce the amount of time that the valve 28 needs be held open, and thereby conserve battery power. Alternatively, it may be possible to use a longer unit dose period ($t_{i,j}$) when using a non-zero $Q_{i,j\ close}$ flow rate, and thereby reduce battery consumption by reducing the total number of unit dose periods. In cases when $Q_{i,j\ close}$ is zero the equation simplifies to, $$S_i = C * \sum_{j=1}^{n} t_{i,j\ open} * Q_{i,j\ open}$$

In a preferred embodiment, the unit dose period ($t_{i,j}$) is pre-determined, and $t_{i,j\ open}$ is calculated to effect the desired agent delivery. Those skilled in the art will readily recognize that it is possible to obtain the same effect by pre-determining $t_{i,j\ open}$ and calculating $t_{i,j\ close}$, and thereby calculating $t_{i,j}$ so that effectively $t_{i,j\ open}$ is held constant while $t_{i,j}$ is varied.

The duration of the unit dose periods ($t_{i,j}$) is so chosen so that they are: (i) short enough that the flow parameters (ΔP) and (R) are unlikely to change significantly so that the flow rates $Q_{i,j\ open}$ and $Q_{i,j\ close}$ can be approximated as being constant over the unit dose period ($t_{i,j}$); (ii) short enough that the open/close flow rate changes are pharmacologically imperceptible or insignificant; and (iii) long enough to achieve acceptable levels of battery consumption (by minimizing the number of battery-consuming opening and closing cycles for the valve 28).

The above algorithms are maintained in non-volatile memory 32, and RAM 34 is used as a work space for at least the purposes of the above calculations. The controller 30 is further coupled to an internalized power source 36.

Figure 3:
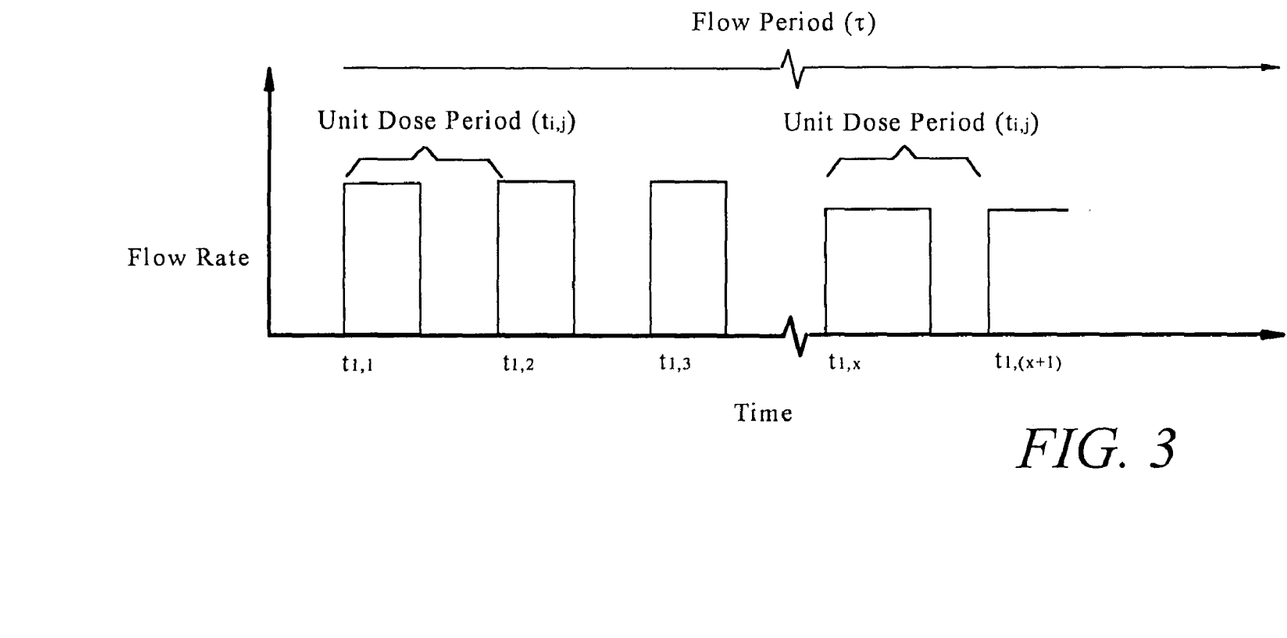
FIG. 3 illustrates an exemplary timing chart corresponding to valve control for regulating a delivery of infusate from an infusate reservoir of the implantable infusion device of either FIG. 2A, 2B, or FIG. 2C.

Reference is hereby made to FIG. 3, which illustrates but one example of the control signals delivered from the controller 30 to the valve 28. The illustrated signals extend over a period of time in which the potential output flow rate decreases. For the exemplary illustrated unit dose periods ($t_{i,j}$), the duration of $t_{i,x\ open}$ is increased relative to the duration of, for example, $t_{i,1\ open}$ for the "initial" dose periods ($t_{i,j}$). Notwithstanding, the duration of the unit dose period ($t_{i,m}$=$t_i$ for all of m) is held constant. Of course, the noted change in $t_{i,j\ open}$ compensates for the change in infusate flow rate without express regard for the reason for such change in flow rate.

In some devices the pressure generated by the drive source 16 will vary according to the volume of infusate remaining in the infusate reservoir 12. For example, in many devices the reservoir pressure drops as the reservoir volume is nearly depleted and rises as the reservoir volume nears (or exceeds) its rated capacity. In conventional infusion devices this is a liability because it affects and therefore reduces the flow rate accuracy and the usable volume of the infusate reservoir 12. However, in the present invention this information can be an asset that is used: (1) in the case of filled reservoirs, to alert a user so as to prevent a dangerous or undesirable overfilling of the pump; and/or (ii) in the case of nearly depleted reservoirs, to measure the volume of fluid remaining in the infusate reservoir 12 by measuring the reservoir pressure, and if appropriate, alert a user that the device should be refilled. As described earlier, the controller can use this information to adjust the open/close cycles, and thereby extend the usable volume of the infusion device without changing the physical size of the device.

In some clinical applications, the duration of the flow period (τ) can be limited by the compatibility or stability of an active agent in the infusate. "Compatibility" and "stability" are terms that are intended to capture all of the changes that can occur in the chemical, physical, pharmacological, or therapeutic properties of an infusate as it resides inside the infusate reservoir 12 of the drug delivery device. While not exhaustive, these changes include: (i) a decrease in the potency of the active ingredient; (ii) an increase in the potency of the active ingredient; and (iii) a change in infusate viscosity. For example, the potency of morphine sulfate in conventional implantable infusion pumps is known to decrease by about 20% over a 90 day period, thus the lack of morphine stability restricts the maximum flow period for this agent to less than about 90 days (without regard to a potential volumetric capacity of the delivering infusion device). This fact, as well as the fact that some conventional constant flow implantable infusion pumps flow faster when full then they do when nearly empty, means that the actual drug dose received by the patient can vary dramatically over a flow period (τ).

However, in the present invention look up tables or algorithms can be used to compensate for known changes in the properties of the infusate to adjust the flow controller over the course of the flow period (τ). This has at least two beneficial effects: (i) a more uniform amount of active agent is administered throughout the flow period (τ), thereby improving therapy and/or reducing side effects; and (ii) the maximum duration of the flow period (τ) can be extended so that more of the infusate reservoir can be used.

For any internally powered, implantable device, the life span of its power source dictates its functional life. Of course, removal and replacement of such device can be traumatic, required to undergo a surgical procedure to effect such removal and replacement. As the benefits of any such implantable device are carefully weighed against the costs of use/replacement (e.g., hardware expense, physician time, hospitalization, etc.) as well as patient morbidity/mortality, it is imperative that efforts be made to provide an implantable device capable of sustaining sufficient operational life but remain cost and size effective. Even when the device incorporates a rechargeable power source (e.g., battery, capacity, etc.) minimizing power consumption is desirable.

System power consumption is largely dictated by the power consumed to actuate the valve 28 through each open-close cycle for each unit dose ($d_{i,j}$) and generally, to a lesser extent, by that required to make the measurements and calculations required to control the valve timing. It is an objective of the present invention to safely minimize and control a total current drain associated with the operation of the valve 28. This control increases the predictability of a life-span of a power source (36, FIGS. 2A, 2B, and 2C). A generalized equation for current drain resulting from valve actuation for one unit dose cycle ($t_{i,j}$) is.

$$I_{total}=I_{open}+I_{held\ open}\cdot t_{i,j\ open}+I_{close}+I_{held\ close}\cdot t_{i,j\ close}$$

where, for a bi-stable valve, $I_{held\ open}$ and $I_{held\ close}$ are zero values, thus $I_{total}=I_{open}+I_{close}$; and by comparison, for a mono-stable valve, $I_{close}$ and $I_{held\ close}$ are likely zero values, thus $I_{total}=I_{open}+I_{held\ open}\cdot t_{i,j\ open}$.

From the above examples, it can be readily seen that system current drain can be easily approximated from the operative nature of a selected valve, wherein the basis for valve selection depends upon an intended application.

Shortening the duration of the unit dose period ($t_{i,j}$) improves flow accuracy, but at the expense of additional battery consumption to effect incremental valve actuation, computations, and pressure and/or temperature measurements. It will also be readily apparent that for reasons of battery conservation, there may be times and conditions within a given flow period (τ) when the prescribed dose period ($T_i$) and/or unit dose period ($t_{i,j}$) should be lengthened or shortened, and that based on the design of the device it may be possible to predetermine these times (such as when the infusate reservoir is nearly empty), or to determine them in real time based on the input from a sensor. For example, when the reservoir is nearly depleted, ΔP may change quickly meaning that the unit dose period ($t_{i,j}$) should be shortened to improve flow accuracy. Doing so, also effectively increases the amount of fluid from the infusate reservoir 12 that can be delivered within flow accuracy specifications (i.e., the usable volume), which is a very desirable feature.

Based on a flow rate determined by the controller 30, an accurate, dynamic calculation of remaining power source life can be made. Likewise, an estimated life for the power source 36 can be approximated from anticipated changes of the infusion device, or the present invention can be configured to pass calculated, real-time information outside the patient to an external controller 50. For this concept, reference is made to FIG. 4, which illustrates a second embodiment of the present invention.

Figure 4:
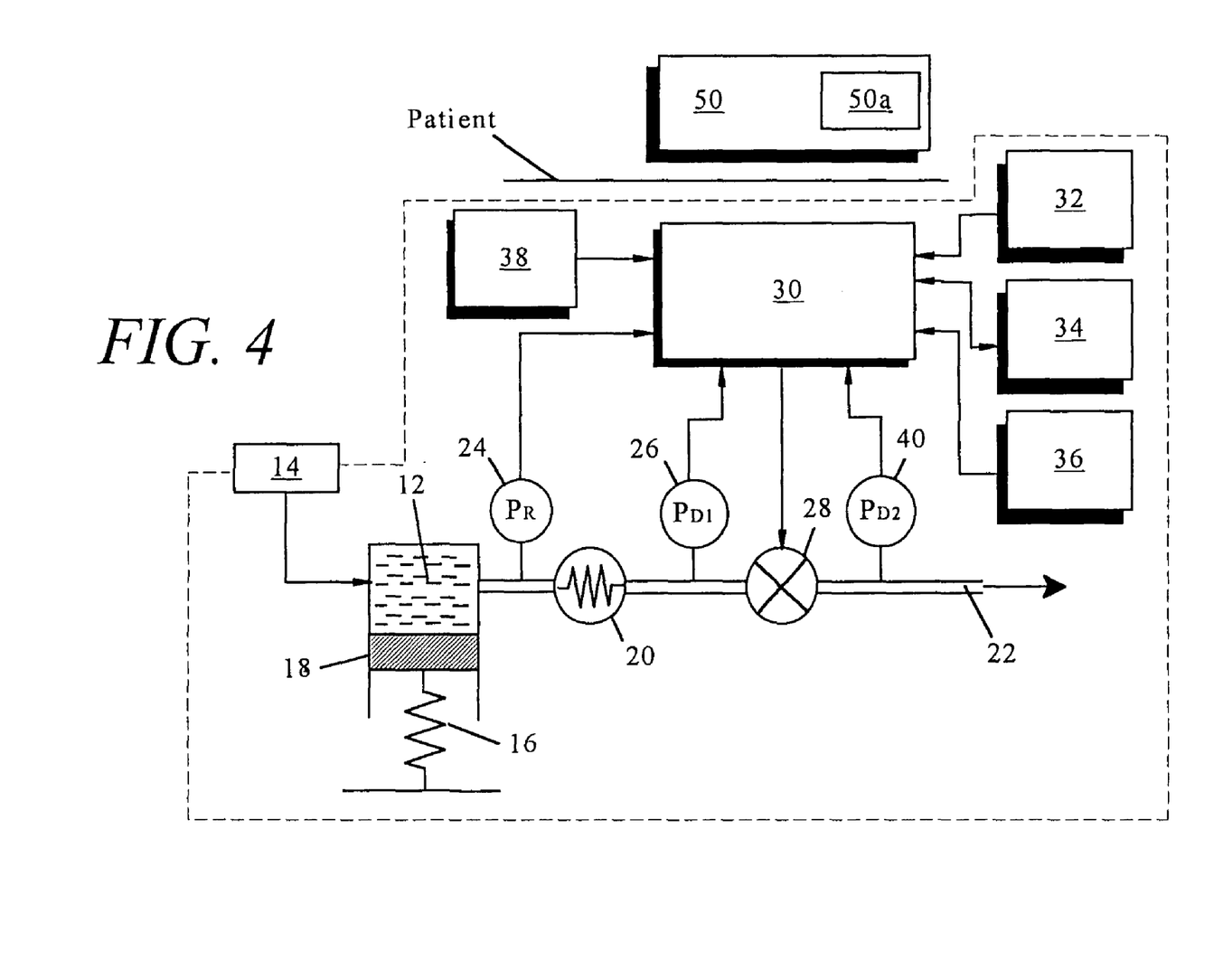
FIG. 4 schematically illustrates an implantable infusion device in accordance with another embodiment of the present invention.
Figure 5:
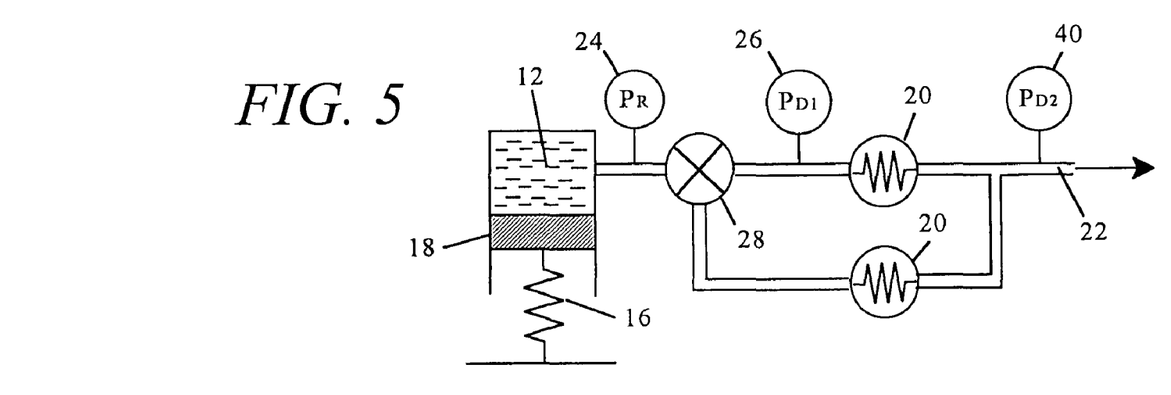
FIG. 5 partially illustrates a schematic representation of an implantable infusion device in accordance with another embodiment of the present invention.
Figure 6:
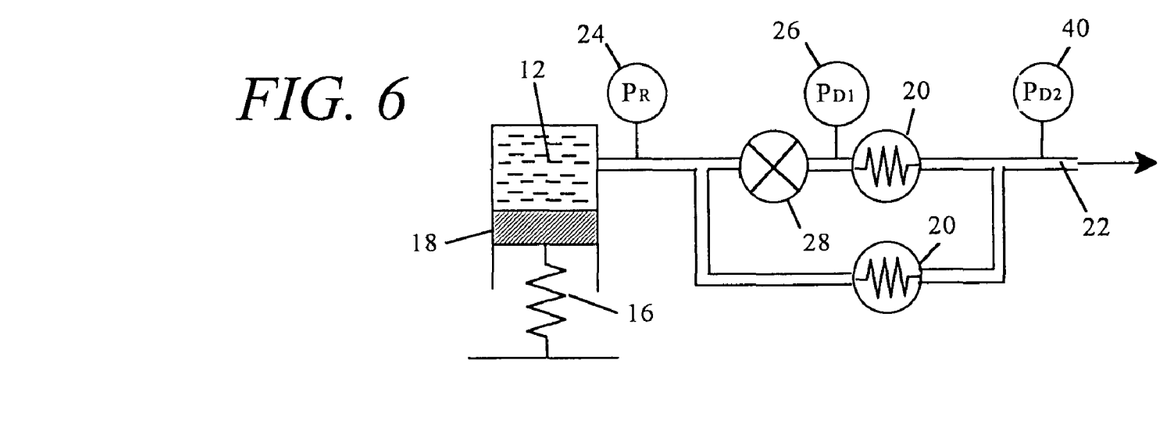
FIG. 6 partially illustrates a schematic representation of an implantable infusion device in accordance with another embodiment of the present invention.
Figure 7:
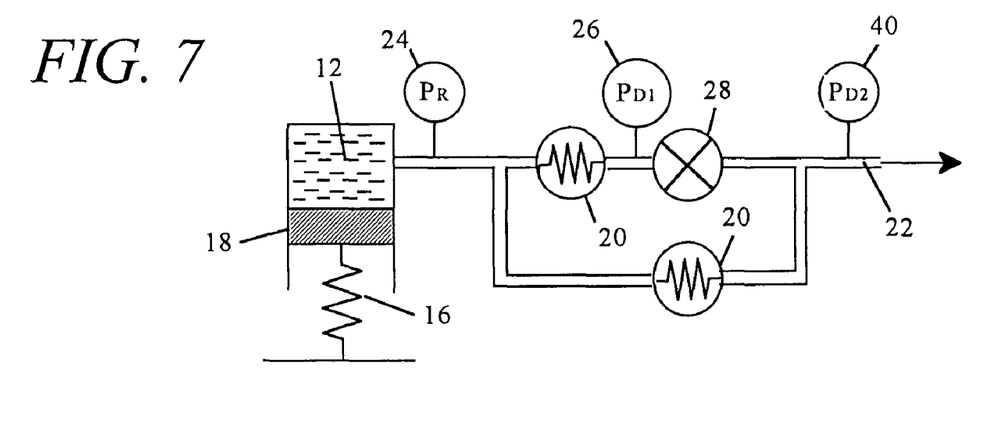
FIG. 7 partially illustrates a schematic representation of an implantable infusion device in accordance with another embodiment of the present invention.
Figure 8:
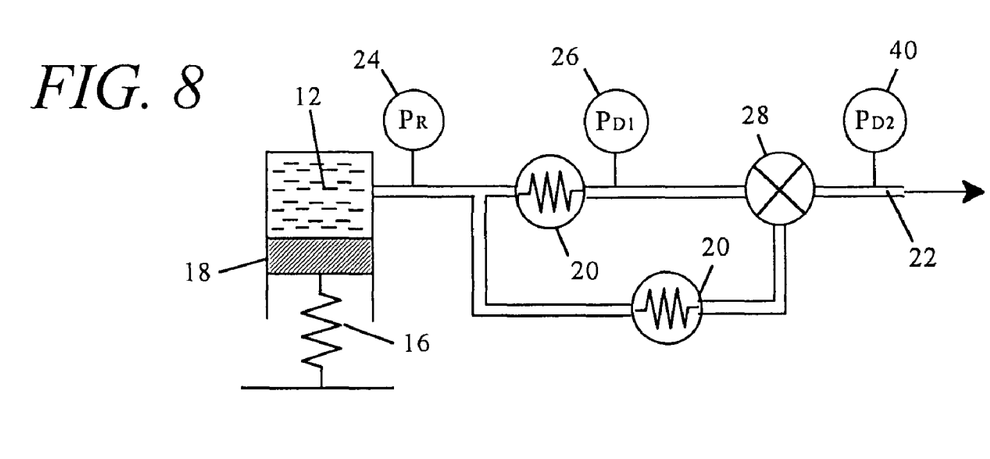
FIG. 8 partially illustrates a schematic representation of an implantable infusion device in accordance with another embodiment of the present invention.
Figure 9:
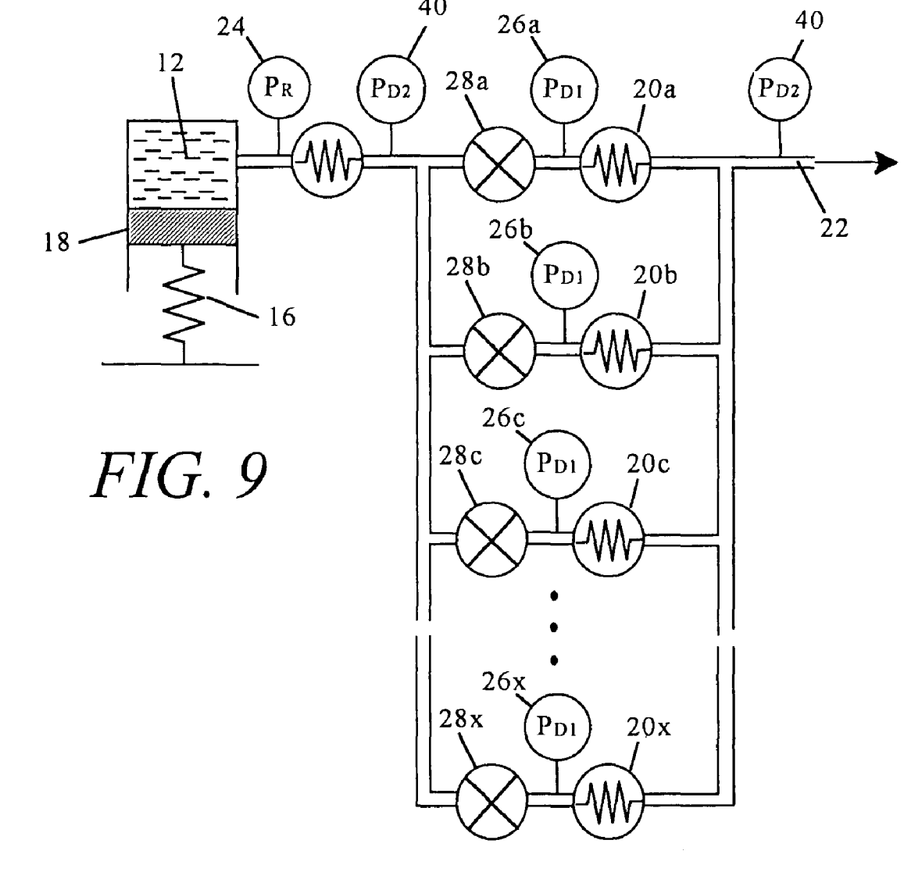
FIG. 9 partially illustrates a schematic representation of an implantable infusion device in accordance with another embodiment of the present invention.
Figure 10:
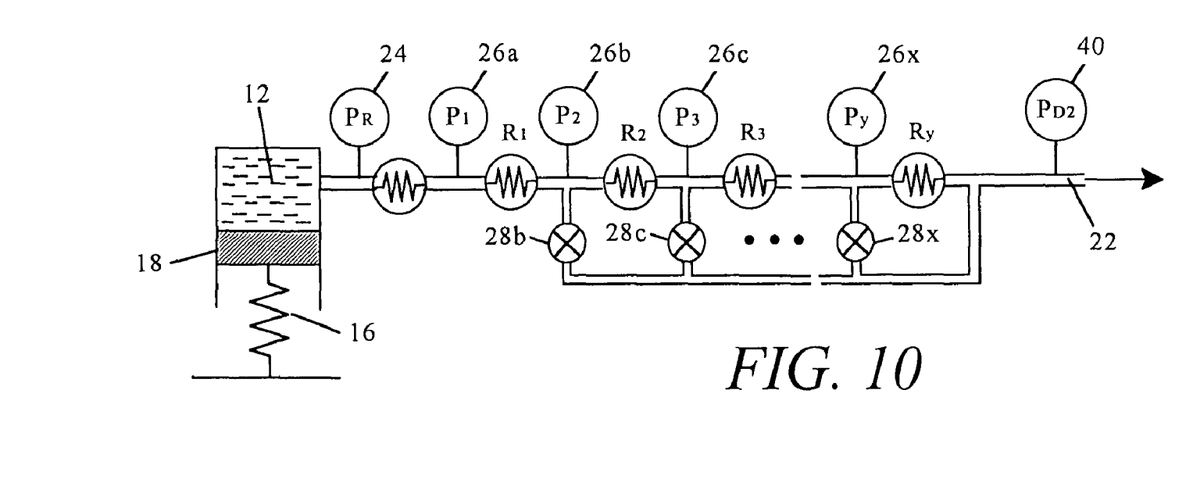
FIG. 10 partially illustrates a schematic representation of an implantable infusion device in accordance with another embodiment of the present invention.
Figure 11:
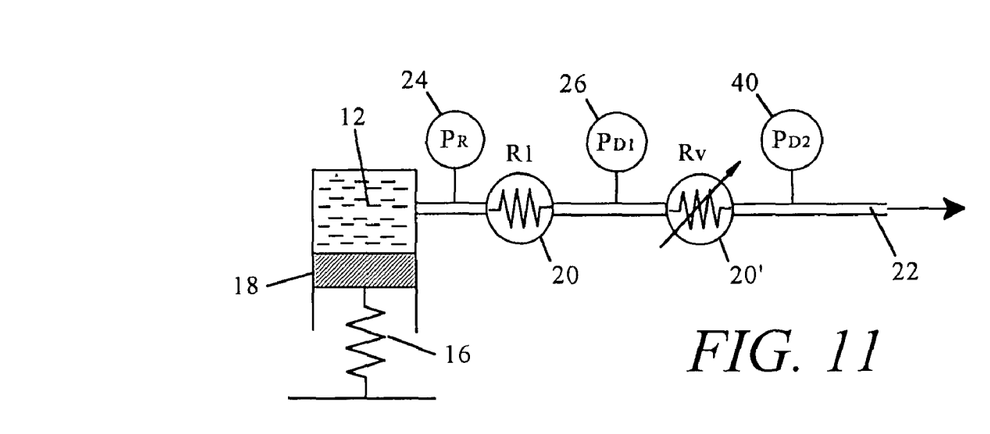
FIG. 11 partially illustrates a schematic representation of an implantable infusion device in accordance with another embodiment of the present invention.

Controller 50 communicates with the controller 30 through a patient's skin. Such communication is made, for example, using common radio-frequency technology that is well known in the art. The manner and form of communication is not critical. Any means (e.g., IR, direct connection, etc.) that is capable of establishing a data transfer link, provided that the controller 50 and the implantable infusion device are provided with the proper link components, is consistent with this aspect of the disclosed invention.

The controller 50 can provide information (e.g., software updates, modification of calculation variables, for example, the unit dose period ($t_{i,j}$), $t_{i,j\ open}$ etc.) to the controller 30 for maintaining accurate functionality of the infusion device. Moreover, the controller 50 can provide instructions to the controller 30 to change any of these variables in response to changes in other parameters, e.g., complex continuous infusion. The controller 50 could also transmit power to the power source 36, if the power source 36 was of a rechargeable nature. Further yet, the controller 50 could transmit power directly to the controller 30 via a carrier signal, e.g., using a radio-frequency carrier signal.

It is contemplated that through the communication link between the controller 30 and the controller 50, data can be uploaded from the controller 30 to the controller 50. To this end, the controller 50 preferably includes a display 50a, which can communicate information, e.g., life expectancy of the power source 28, to a user for real-time consideration. Additionally, diagnostic information regarding the operability of the implantable infusion device can be supplied to the user with only slight modification to the system illustrated in FIG. 2A.

In further reference to FIG. 4, an infusion device in accordance with the present invention could be provided with a third pressure sensing device 40, which is positioned downstream of the valve 28. Further yet, additional variations of the specific arrangement of the components of this system are illustrated in FIGS. 5-11.

From the initial pressure sensing devices 24 and 26 (and the optional third pressure sensing device 40), the following information can be gathered and supplied back to a monitoring user via a data link between the controller 30 and the controller 50:

Valve open, if $P_R > P_{D1} \cong P_{D2}$;

Valve closed, if $P_R \cong P_{D1} > P_{D2}$;

Catheter obstruction (e.g., kink, thrombosis), if $P_R \cong P_{D1} \cong P_{D2}$ Further yet, transient responses from the second pressure sensing device 26 and the third pressure sensing device 40 during or proximate to an opening or closing of the valve 28 can be monitored to provide information regarding a system status. For example, in reference to the exemplary embodiment illustrated in FIG. 4, if prior to opening the valve 28, $P_R \cong P_{D1} \geq P_{D2}$, then as the valve 28 is opened, a measured pressure transient enables a calculated appreciation of how freely infusate is able to flow through the catheter 22 and the flow restrictor 20. The rate of change of pressures $P_{D1}$ and $P_{D2}$ will communicate whether or not certain parts of the flow path are obstructed (e.g., completely or in part), and if obstructed, the location of such obstruction relative to the flow path. Moreover, as the valve 28 is closed, a measured pressure transient (between $P_{D1}$ and $P_{D2}$) will allow an inference as to how freely infusate is able flow form the infusate reservoir 12 through at least the restrictor 20. A rate of change of pressure will communicate whether the system filter positioned between the infusate reservoir 12 and the restrictor 20) or the restrictor 20 is partially or completely obstructed as might occur over the lifetime of the device. Of course, this information could be displayed on the display 50a. In a like manner, as the valve 28 is closed, a pressure transient measured for Pot will allow an inference as to how freely infusate is able to flow through the delivery catheter 22.

Provided that the critical portion of the flow path (i.e., that portion through which regardless of any/all valve states all infusate must flow) within the infusion device 10 is not completely occluded, the data gained from the aforementioned detected conditions can enable a modification of controller variables (e.g., the unit dose period ($t_{i,j}$), $t_{i,j\ open}$, etc.) so as to enable a targeted dosage/delivery rate to be maintained. The information gained can also provide the managing clinician with valuable information to help determine whether or not surgical intervention or a change in dosage is required.

As should also be noted, while the controller 50 has been described as a device capable of establishing a data transfer link, it should be further noted that modification of at least calculation variables (e.g., the unit dose period ($t_{i,j}$), $t_{i,j\ open}$, etc.) can be accomplished through other non-invasive methods (e.g., trocar).

While the invention has been described herein relative to a number of particularized embodiments, it is understood that modifications of, and alternatives to, these embodiments, in particular, variants in the number, type, and configuration of the flow restrictor(s), valve(s), and sensor(s), such modifications and alternatives realizing the advantages and benefits of this invention, will be apparent those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A method for infusing a fluid in a living body, said method comprising:
   providing a reservoir, a flow restrictor, and a valve in an implantable drug pump device;
   transiently storing fluid infusate in said reservoir for transmission to a delivery site after the implantable drug pump device has been implanted in a patient;
   limiting a flow rate of the fluid infusate using said flow restrictor disposed in a fluid path between said reservoir and said delivery site;
   determining transient pressure differentials relative to said flow restrictor by a controller component of the implantable drug pump;
   determining whether an occlusion is present in the flow path using the transient pressure differentials, the transient pressure differentials being determined when the controller component closes a valve to interrupt flow of the fluid infusate from the implantable drug pump device;

determining a location of an occlusion when an occlusion is detected using the transient pressure differentials;

controlling said valve disposed in said fluid path between said reservoir and said delivery site to control infusate output from said reservoir to said delivery site as a function of said transient pressure differentials across said flow restrictor, wherein the controlling said valve automatically responds to a detection of a partial occlusion by altering a unit dose period for delivery of the fluid infusate;

communicating a signal, from implantable drug pump device to an external device, that is indicative of an amount of occlusion detected by the controller; and communicating a signal, from implantable drug pump device to an external device, that is indicative of a location of the occlusion.

2. The method of claim 1, wherein controlling said valve comprises:

subdividing a flow period into smaller unit dose periods over which a pressure differential across said flow restrictor is likely to remain constant and controlling said valve to deliver a total dose of said infusate through a series of said unit dose periods.

3. The method of claim 2, wherein said unit dose periods are selected at least in part to reduce battery consumption.

4. The method of claim 2, wherein said unit dose periods are selected so that an open/close rate of said valve is pharmacologically insignificant.

5. The method of claim 1, further comprising:

determining a rate at which a pressure differential across said flow restrictor changes.

6. The method of claim 5, wherein controlling said valve comprises:

altering timing of a period of said valve being opened as a function of said rate at which a pressure differential across said flow restrictor changes.

7. The method of claim 1, further comprising:

providing an alert with respect to overfilling of said reservoir using a pressure differential across said flow restrictor.

8. The method of claim 1, further comprising:

providing an alert with respect to depletion of said reservoir using a pressure differential across said flow restrictor.

9. The method of claim 1, further comprising:

determining a temperature of said infusate, wherein controlling said valve comprises controlling infusate output from said reservoir as a function of said temperature of said infusate.

* * * * *